(12) United States Patent
Saruwatari et al.

(10) Patent No.: US 7,956,229 B2
(45) Date of Patent: Jun. 7, 2011

(54) METHOD FOR PRODUCING INTERNAL OLEFIN, INTERNAL OLEFIN MIXTURE, AND OIL DRILLING FLUID CONTAINING INTERNAL OLEFIN MIXTURE

(75) Inventors: Tetsuya Saruwatari, Chiba (JP); Hideki Yamane, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 726 days.

(21) Appl. No.: 11/813,727

(22) PCT Filed: Dec. 28, 2005

(86) PCT No.: PCT/JP2005/024029
§ 371 (c)(1),
(2), (4) Date: Jul. 11, 2007

(87) PCT Pub. No.: WO2006/075526
PCT Pub. Date: Jul. 20, 2006

(65) Prior Publication Data
US 2008/0167510 A1   Jul. 10, 2008

(30) Foreign Application Priority Data
Jan. 12, 2005   (JP) ................................. 2005-004828

(51) Int. Cl.
*C07C 5/23* (2006.01)
(52) U.S. Cl. ........ 585/664; 585/666; 585/667; 585/668; 585/669

(58) Field of Classification Search ........... 585/664–670
See application file for complete search history.

(56) References Cited

U.S. PATENT DOCUMENTS
6,054,629 A * 4/2000 Baralt et al. .................. 585/670

FOREIGN PATENT DOCUMENTS

| EP | 1 795 572 A1 | 6/2007 |
|---|---|---|
| JP | 10 167992 | 6/1998 |
| JP | 2004-285000 | 10/2004 |
| WO | 90 03354 | 4/1990 |
| WO | WO 01/32590 A2 | 5/2001 |

OTHER PUBLICATIONS

U.S. Appl. No. 11/574,558, Mar. 1, 2007, Saruwatari, et al.

* cited by examiner

*Primary Examiner* — Tam M Nguyen
(74) *Attorney, Agent, or Firm* — Oblon, Spivak, McClelland, Maier & Neustadt, L.L.P.

(57) ABSTRACT

A method for producing an internal olefin by stably isomerizing an α-olefin by using an inexpensive zeolite catalyst while preventing an oligomerization reaction is provided. The method for producing an internal olefin comprises a step of isomerizing an α-olefin having from 16 to 18 carbon atoms by passing through a zeolite catalyst bed, wherein the α-olefin having from 16 to 18 carbon atoms is circulated through and brought into contact with the zeolite catalyst bed before starting the isomerization reaction.

16 Claims, No Drawings

METHOD FOR PRODUCING INTERNAL OLEFIN, INTERNAL OLEFIN MIXTURE, AND OIL DRILLING FLUID CONTAINING INTERNAL OLEFIN MIXTURE

TECHNICAL FIELD

The present invention relates to a method for producing an internal olefin by isomerizing an α-olefin having from 16 to 18 carbon atoms, to an internal olefin mixture and to a base oil for petroleum drilling oils containing an internal olefin mixture.

BACKGROUND ART

Internal olefins have hitherto been used or various applications, concretely a base oil for petroleum drilling oils, a raw material of detergents, a raw material of paper sizing agents, a base oil or raw material of lubricating oils, a raw material of chemical products, and the like. For example, though α-olefins having 14 carbon atoms are used as a base oil for petroleum drilling oils, when released in the environment the α-olefins having 14 carbon atoms exhibit fish toxicity, and therefore, in the case of a submarine oilfield, it is considered to be preferable to use α-olefins having 16 or more carbon atoms. However, since the α-olefins having 16 or more carbon atoms are inferior in fluidity to the α-olefins having 14 carbon atoms, it is necessary that they are internally isomerized to improve the fluidity.

In the case of performing an internal isomerization reaction of an α-olefin, it is important to prevent the formation of branched olefins. Similar to the problems in the field of surfactants, this is because the branched olefins are poor in biodegradability so that they remain in the environment over a long period of time. Then, there have been filed some patent applications regarding technologies for preventing a skeletal isomerization reaction so that only an internal isomerization reaction of an α-olefin is selectively performed. Though there is no definite index on how extent the skeletal isomerization should be prevented, for example, it is disclosed that a rate of skeletal isomerization reaction is controlled to less than 5% (see, for example, Patent Document 1).

In the internal isomerization reaction of an α-olefin using a zeolite catalyst, as a method for preventing the skeletal isomerization reaction, there are disclosed a method for using a pentasil zeolite catalyst containing from 1 to 10% by weight of nickel monoxide as a promoter (see, for example, Patent Document 1); and a method for using an alumino-phosphate-containing molecular sieve with one-dimensional pores having a diameter of from 3.8 to 5.0 angstroms as a catalyst (see, for example, Patent Document 2).

In the case of performing the internal isomerization reaction of an α-olefin, another important point resides in the matter that an oligomer is not formed in the reaction. When an oligomer increases, it is easily supposed that the fluidity of a formed internal olefin is deteriorated, and it is desired to suppress the formation of an oligomer as much as possible.

In claim 8 of Patent Document 1, it is described that a residual α-olefin is controlled to less than 5%, and in Example 3 thereof, it is actually proven that in isomerizing an α-olefin having 18 carbon atoms, the amount of formation of an olefin having 36 carbon atoms is controlled at not more than 4%.

In the light of the above, in order to improve the fluidity of an internal olefin, it is devised to reduce an oligomer at a 1% unit. However, it is still hard to say that the reduction of an oligomer is sufficient, and there may be the case where for the purpose of making the concentration of an oligomer low, the reaction product liquid must be further distilled.

Accordingly, a method for producing an internal olefin by stably isomerizing an α-olefin while preventing an oligomerization reaction is desired.

Patent Document 1: U.S. Pat. No. 6,054,629
Patent Document 2: U.S. Pat. No. 6,281,404

DISCLOSURE OF THE INVENTION

Problems that the Invention is to Solve

Under the foregoing circumstances, the present invention has been made and is aimed to provide a method for producing an internal olefin by stably isomerizing an α-olefin by using an inexpensive zeolite catalyst while preventing an oligomerization reaction.

Means for Solving the Problems

In order to solve the foregoing problems, the present inventors made extensive and intensive investigations. As a result, it has been found that by circulating a starting α-olefin into a zeolite catalyst bed before starting an isomerization reaction, the oligomerization reaction activity can be largely reduced and that by the foregoing circulation, an internal olefin with more excellent fluidity can be produced without performing distillation. The present invention has been accomplished on the basis of such knowledge.

That is, the present invention is to provide a method for producing an internal olefin, an internal olefin mixture and a base oil for petroleum drilling oils containing an internal olefin mixture.

(1) A method for producing an internal olefin, comprising a step of isomerizing an α-olefin having from 16 to 18 carbon atoms by passing through a zeolite catalyst bed, an α-olefin having from 16 to 18 carbon atoms being circulated through and brought into contact with the zeolite catalyst bed before starting the isomerization reaction.

(2) The method for producing an internal olefin as recited in (1) above, wherein the zeolite catalyst is an MFI type zeolite.

(3) The method for producing an internal olefin as recited in (1) or (2) above, wherein the total amount of the α-olefin to be circulated is from 1 to 20 times of the zeolite catalyst by volume.

(4) The method for producing an internal olefin as recited in any one of (1) to (3) above, wherein an LHSV (liquid hourly space velocity) of the α-olefin to be circulated is from 0.1 to 10 $h^{-1}$.

(5) The method for producing an internal olefin as recited in any one of (1) to (4) above, wherein a temperature of the catalyst bed at the circulation of the α-olefin is from 70 to 180° C.

(6) The method for producing an internal olefin as recited in any one of (1) to (5) above, wherein a circulation time of the α-olefin is from 1 to 100 hours.

(7) An internal olefin mixture having from 16 to 18 carbon atoms obtained by the method recited in any one of (1) to (6) above.

(8) A base oil for petroleum drilling oils containing the internal olefin mixture having from 16 to 18 carbon atoms as recited in (7) above.

Effect of the Invention

According to the present invention, the oligomerization reaction activity of the zeolite catalyst bed can be largely reduced, and an internal olefin with good fluidity can be produced stably with good efficiency and advantageously from the industrial viewpoint.

BEST MODES FOR CARRYING OUT THE INVENTION

The starting α-olefin of the present invention is an x-olefin having from 16 to 18 carbon atoms. Though a proportion (mass ratio) of an α-olefin having 16 carbon atoms to an O-olefin having 18 carbon atoms in the starting α-olefin is not particularly limited, it is usually from 20/80 to 5/65, and preferably from 25/7 to 32/68.

This α-olefin having from 16 to 18 carbon atoms can be obtained by distilling a low polymer which is preferably resulted from lowly polymerizing ethylene by using a Ziegler type catalyst. This oligomer is a mixture of 1-butene, 1-hexene, 1-octene, 1-decene 1-dodecene, 1-tetradecene, 1-hexadecene, 1-octadecene, 1-eicosene, and the like.

In addition, the α-olefin which is used in the present invention can also be obtained by distilling an α-olefin obtained from a catalytic cracking apparatus or the like.

Examples of the zeolite catalyst which is used in the present invention include natural zeolites and synthetic zeolites. Examples of the natural zeolite include chabazite, mordenite, erionite, faujasite, and clinoptilolite. Examples of the synthetic zeolite include an A type, a B type, an X type, a Y type, an omega type, and an MFI type. Of these, an MFI type is preferable; and ZSM-5 or the like is suitable as the MFI type. A proton type zeolite resulting from substitution of a part or the whole of cations is especially preferable and above all, proton-substituted H-ZSM-5 is preferable.

In the method for producing an internal olefin of the present invention, before starting the isomerization reaction, the starting α-olefin having from 16 to 18 carbon atoms is circulated through and brought into contact with the zeolite catalyst bed. The amount of the α-olefin which is used for this circulation is preferably from 1 to 20 times, and more preferably from 3 to 10 times of the zeolite catalyst by volume. When the amount of the x-olefin which is used for the circulation is 1 or more times of the zeolite catalyst by volume, an effect for reducing the oligomerization reaction activity of this catalyst is exhibited; and when the amount of the α-olefin is 20 times or less, it is economically practical.

Considering the reducing effect of the oligomer reaction activity of the zeolite catalyst bed and the like, an LHSV liquid hourly space velocity) of the α-olefin during the foregoing circulation is usually from approximately 0.1 to 10 $h^{-1}$, and preferably from 1 to 5 $h^{-1}$.

A temperature of the zeolite catalyst bed at the circulation of the α-olefin is usually from approximately 70 to 180° C., and preferably from 100 to 160° C. From the standpoint of a good balance between the reducing effect of the oligomer reaction activity of the zeolite catalyst bed and the economy, the circulation time of the α-olefin is usually from approximately 1 to 100 hours, and preferably from 4 to 48 hours.

In the present invention, as described previously, the α-olefin having from 16 to 18 carbon atoms is isomerized by passing through the zeolite catalyst bed having an α-olefin circulated therethrough and brought into contact therewith, thereby producing an internal olefin. In that case, the α-olefin used for the foregoing circulation can be used as a raw material. A temperature of the isomerization reaction is usually from approximately 70 to 180° C. and preferably from 100 to 160° C.

A reaction mode is not particularly limited and may be any of a fixed bed circulation type or a batch type (including a continuous type stirring tank). A pressure is usually from approximately atmospheric pressure to 5 MPa, and preferably from atmospheric pressure to 1 MPa. In the case where the reaction mode is a fixed bed circulation type, considering an α-olefin conversion rate and productivity, an LHSV (liquid hourly space velocity) of the α-olefin is usually selected from the range of from approximately 0.1 to 10 $h^{-1}$, and preferably from 1 to 4 $h^{-1}$.

Also, in the case where the reaction mode is a batch type, the amount of used amount of the zeolite catalyst is usually in the range of from 1 to 60 parts by mass, preferably from 10 to 50 parts by mass, and more preferably from 20 to 40 parts by mass based on 100 parts by mass of the starting α-olefin. In that case, though a reaction time varies depending upon the reaction temperature and the desired α-olefin conversion rate and cannot be determined indiscriminately, it is usually from approximately 30 minutes to 20 hours, and preferably from approximately 1 to 10 hours.

In the light of the above, by using the zeolite catalyst having the starting α-olefin circulated therethrough and brought into contact therewith before starting the isomerization reaction, the α-olefin can be internally isomerized at a conversion rate of 90% or more under a relatively mild condition. Moreover since it is possible to prevent the deterioration of the catalyst and undesired side-reactions such as skeletal isomerization reaction and oligomerization reaction, the desired internal olefin is selectively obtained.

Also, since commercial product can be obtained without performing distillation purification of the reaction product liquid, a distillation column for the removal of the oligomerization reaction product or the like becomes unnecessary, and therefore the method is highly economical. Also, since the zeolite catalyst which is used in the present invention is generally inexpensive, it is possible to design a sufficiently economical process even on the assumption that the catalyst is exchanged.

Also, the present invention is to provide an internal olefin mixture obtained by the foregoing method and a base oil for petroleum drilling oils containing this internal olefin mixture.

EXAMPLES

Next, the present invention is described below in more detail with reference to the Examples. However, it should be construed that the present invention is not limited to these Examples in any way.

Comparative Example 1

A stainless steel-made reaction column having a diameter of 12 mm (length: 1.1 m, inside diameter: 10 mm) was filled with 50 mL of HMFI-90 (a proton type MFI zeolite catalyst, manufactured by Sud-Chemie), and the inside of the reaction column was purged with nitrogen. A mixture of 70% by mass of an α-olefin having 16 carbon atoms (C16) and 30% by mass of an α-olefin having 18 carbon atoms (C18) was fed by an up-flow at 100 mL/h into this reactor. The reaction was continued while increasing the reaction temperature as the catalyst activity decreases, such that the conversion rate of the α-olefin became 93 to 95% or more. After 24 hours, the catalyst activity was stable, and the reaction temperature at that time was 130° C.

At a point of time of elapsing 48 hours since starting the feed of the α-olefin, the reaction temperature was 130° C.; and the isomerization conversion rate of a double bond was 94% for the C16-olefin and 93% for the C18 α-olefin, respectively. Also, an oligomer concentration in the formed liquid was 2.1% by mass. In addition, the kinematic viscosity of the resulting internal olefin was measured at 0° C. by using a Cannon-Fenske viscometer, thereby evaluating the fluidity. These results are shown in Table 1.

Example 1

The same operations up to purging the inside of the reaction column with nitrogen as in Comparative Example 1 were repeated. Thereafter, 300 mL of a mixture of 70% by mass of a C16 α-olefin and 30% by mass of a C18 α-olefin was circulated and contacted by an up-flow at 100 mL/hr for 24 hours in the reactor. During this circulation, the LHSV of the α-olefin was 2 h$^{-1}$, and the temperature of the zeolite catalyst bed was 150° C.

Next the foregoing circulation was stopped; subsequent to the foregoing 300 mL α-olefin mixture, the same α-olefin mixture was fed by an up-flow at 100 mL/h; and the reaction was continued while increasing the reaction temperature as the catalyst activity decreases such that the conversion rate of the α-olefin became 93 to 935% or more. After 24 hours the catalyst activity was stable, and the reaction temperature at that time was 13° C.

After stopping the circulation, at a point of time of elapsing 48 hours since starting the feed of the α-olefin the reaction temperature was 135° C.; and the isomerization conversion rate of a double bond was 95% for the C16 α-olefin and 93% for the C18-olefin, respectively. Also, an oligomer concentration in the formed liquid was 1.2% by mass, and the oligomer formation activity was reduced by half as compared with Comparative Example 1. In addition, the fluidity of the obtained internal olefin was evaluated in the same method as described above. These results are shown in Table 1.

TABLE 1

| | Isomerization conversion rate (%) | | Oligomer concentration | |
|---|---|---|---|---|
| | C16 α-olefin | C18 α-olefin | (% by mass) | Fluidity |
| Example 1 | 95 | 93 | 1.2 | Good |
| Comparative Example 1 | 94 | 93 | 2.1 | Poor |

(Note)
Fluidity:
Good: The kinematic viscosity at 0° C. is less than 8.0 mm$^2$/s.
Poor: The kinematic viscosity at 0° C. is 8.0 mm$^2$/s or more.

INDUSTRIAL APPLICABILITY

The internal olefin obtained by the producing method of the present invention is good in fluidity and suitable for applications such as a base oil for petroleum drilling oils.

The invention claimed is:

1. A method for producing an internal olefin comprising:
   circulating through and bringing into contact with a zeolite catalyst bed a α-olefin having from 16 to 18 carbon atoms before starting an isomerization reaction in said zeolite catalyst bed; followed by
   internally isomerizing, in said catalyst bed, the α-olefin to form the internal olefin;
   wherein said zeolite catalyst bed consists essentially of a zeolite.

2. The method for producing an internal olefin according to claim 1, wherein the zeolite catalyst is an MFI type zeolite.

3. The method for producing an internal olefin according to claim 1, wherein the total amount of the α-olefin to be circulated is from 1 to 20 times of the zeolite catalyst by volume.

4. The method for producing an internal olefin according to claim 1, wherein an LHSV (liquid hourly space velocity) of the α-olefin to be circulated is from 0.1 to 10 h$^{-1}$.

5. The method for producing an internal olefin according to claim 1, wherein the temperature of the catalyst bed at the circulation of the α-olefin is from 70 to 180° C.

6. The method for producing an internal olefin according to claim 1, wherein the circulation time of the α-olefin is from 1 to 100 hours.

7. The method for producing an internal olefin according to claim 1, wherein the α-olefin is internally isomerized at a conversion rate of 90% or more.

8. The method for producing an internal olefin according to claim 1, wherein a skeletal isomerization reaction is inhibited.

9. The method for producing an internal olefin according to claim 1, wherein an oligomerization reaction is inhibited.

10. The method for producing an internal olefin according to claim 2, wherein a skeletal isomerization reaction is inhibited.

11. The method for producing an internal olefin according to claim 2, wherein an oligomerization reaction is inhibited.

12. The method for producing an internal olefin according to claim 1, wherein the internal olefin produced according to the method has a kinematic viscosity at 0° C. of less than 8.0 mm$^2$/s.

13. The method for producing an internal olefin according to claim 1, wherein the zeolite catalyst is an H-MFI type zeolite.

14. The method for producing an internal olefin according to claim 2, wherein the MFI type zeolite is ZSM-5.

15. The method for producing an internal olefin according to claim 13, wherein the H-MFI type zeolite is H-ZSM-5.

16. A method for producing an internal olefin comprising:
   circulating through and bringing into contact with a zeolite catalyst bed a α-olefin having from 16 to 18 carbon atoms before starting an isomerization reaction in said zeolite catalyst bed, followed by
   internally isomerizing, in said catalyst bed, the α-olefin to form the internal olefin,
   wherein said zeolite catalyst bed consists of a zeolite.

* * * * *